United States Patent
Vogel et al.

(10) Patent No.: US 11,047,820 B2
(45) Date of Patent: Jun. 29, 2021

(54) FILTER FOR A RESPIRATORY AIR ANALYZER, RESPIRATORY AIR ANALYZER AND METHOD FOR MONITORING A FILTER

(71) Applicant: Robert Bosch GmbH, Stuttgart (DE)

(72) Inventors: Heike Vogel, Kernen im Remstal (DE); Christina Herlt, Waiblingen (DE); Kathy Sahner, Mannheim (DE); Hubert Wittmann, Hirschau (DE)

(73) Assignee: Robert Bosch GmbH, Stuttgart (DE)

( * ) Notice: Subject to any disclaimer, the term of this patent is extended or adjusted under 35 U.S.C. 154(b) by 1012 days.

(21) Appl. No.: 15/145,669

(22) Filed: May 3, 2016

(65) Prior Publication Data
US 2016/0327501 A1 Nov. 10, 2016

(30) Foreign Application Priority Data

May 6, 2015 (DE) ...................... 10 2015 208 443.4

(51) Int. Cl.
*G01N 27/02* (2006.01)
*G01N 33/497* (2006.01)
*A61B 5/08* (2006.01)
*A61M 16/10* (2006.01)
*G01N 1/22* (2006.01)

(52) U.S. Cl.
CPC .......... *G01N 27/026* (2013.01); *A61B 5/082* (2013.01); *A61M 16/105* (2013.01); *G01N 33/497* (2013.01); *A61M 2205/3317* (2013.01); *G01N 1/2205* (2013.01)

(58) Field of Classification Search
None
See application file for complete search history.

(56) References Cited

U.S. PATENT DOCUMENTS

| | | | | |
|---|---|---|---|---|
| 2002/0112605 | A1* | 8/2002 | Motouji | B01D 53/0454 95/8 |
| 2004/0133116 | A1* | 7/2004 | Abraham-Fuchs | G01N 33/0037 600/532 |
| 2010/0133120 | A1* | 6/2010 | Varney | G01N 33/497 205/785.5 |

FOREIGN PATENT DOCUMENTS

| | | | | |
|---|---|---|---|---|
| DE | 38 18 052 A1 | 12/1989 | | |
| DE | 10 2006 008 324 B3 | 4/2007 | | |
| DE | 10 2009 015 562 A1 | 10/2010 | | |
| DE | 10 2013 109 069 A1 | 2/2015 | | |
| EP | 0 231 405 A1 | 8/1987 | | |
| EP | 1 384 069 B1 | 6/2006 | | |
| FR | 2 677 765 A1 | 12/1992 | | |
| FR | 2677765 A1 * | 12/1992 | ........... | A62B 18/088 |
| JP | 2007-262973 A | 10/2007 | | |
| WO | 97/16631 A2 | 5/1997 | | |
| WO | 02/088691 A2 | 11/2002 | | |

* cited by examiner

Primary Examiner — J. Christopher Ball
(74) Attorney, Agent, or Firm — Maginot, Moore & Beck LLP

(57) ABSTRACT

A filter for a respiratory air analyzer includes a filter housing, a converter material, and a sensor arranged in the filter housing. The converter material is arranged in the filter housing between a gas inlet opening and a gas outlet opening. The sensor has a first electrode and a second electrode that are configured to record a characteristic of at least a part of the converter material that is arranged between the first and second electrodes.

15 Claims, 4 Drawing Sheets

FILTER FOR A RESPIRATORY AIR ANALYZER, RESPIRATORY AIR ANALYZER AND METHOD FOR MONITORING A FILTER

This application claims priority under 35 U.S.C. § 119 to patent application no. DE 10 2015 208 443.4, filed on May 6, 2015 in Germany, the disclosure of which is incorporated herein by reference in its entirety.

BACKGROUND

The disclosure is based on a filter for a respiratory air analyzer, a respiratory air analyzer, and a method for monitoring a filter for a respiratory air analyzer.

EP 1384069 B1 concerns the field of respiratory gas analysis. It involves a patient blowing into a device in order to determine the concentration of various gases in the respiratory air.

SUMMARY

Against this background, with the approach presented here a filter for a respiratory air analyzer, a respiratory air analyzer, and a method for monitoring a filter are presented in the disclosure. Advantageous developments and improvements are possible by the measures recited in the dependent claims.

If a characteristic of at least a part of a converter material that is used in a filter can be recorded directly in the filter, a functional state of the converter material, and consequently of the filter, can be inferred from the characteristic recorded.

A filter for a respiratory air analyzer is presented, the filter having the following features:
a filter housing, in which a converter material is arranged between a gas inlet opening and a gas outlet opening; and
a sensor, which is arranged in the filter housing and, for recording a characteristic of at least a part of the converter material, has a first electrode and a second electrode, between which at least a part of the converter material (108) is arranged or can be arranged.

The filter is suitable for use for a respiratory air analyzer, but also for example for an air-conditioning system. A respiratory air analyzer may be understood as meaning a medical device for analyzing constituents of the respiratory air of a patient. The respiratory air may be referred to as respiratory gas. A filter may be a device for removing a specific fraction of a medium. Here, the filter is designed for the purpose of altering at least one constituent of the respiratory air by conversion into at least one modified constituent. A filter housing may be an enclosure of the filter. The filter housing provides the filter with its structural integrity. The gas inlet opening and the gas outlet opening may be referred to as interfaces with the respiratory air analyzer. The filter may have a prescribed direction of flow. The conversion takes place by using the converter material. In the conversion, the constituent of the respiratory air reacts with the converter material. In this process, the constituent is converted and the converter material is consumed. A characteristic may be understood as meaning a feature, for example an electrical property, of the converter material. The characteristic may be dependent on a functional state of the converter material, for example consumed or unconsumed. Consequently, the characteristic of a consumed converter material may differ from the characteristic of an unconsumed converter material. The characteristic may be determined by using the electrodes and be reproduced in an electrical signal. Consequently, the sensor may be designed to provide a signal representing the characteristic, and consequently a functional state, of the converter material. In the filled state of the filter, the electrodes of the filter may be spaced apart from one another by the at least a part of the converter material.

The approach presented here is suitable for applying to such cases in which an analyte is chemically modified before the measurement in the respiratory air analyzer, for example by reduction or oxidation by chemicals that are consumed, such as for example potassium permanganate for the oxidation, referred to hereinafter as the converter. The converter material may consist of the converter or comprise such a converter. In medical products, this method may be preferred to a catalyst, since catalysts usually require high temperatures, which are difficult to implement in the corresponding systems.

Converters for medical applications or for air filtering in air-conditioning systems may be applied to powder or small spheres of silica gel or aluminum oxide in order to increase the surface area.

The converter is consumed, which in the case of repeated use and/or excessive time in use can lead to an incomplete conversion of the analyte, and consequently to a falsification of the measurement result. In order to prevent this incomplete conversion, the converter may be regularly exchanged. Until now, this has been performed for example after x measurements and/or after a time period y. Direct monitoring of whether the converter is still capable of functioning, or an indication as soon as this is at risk, would be advantageous.

The measuring device presented here as being on the filter allows an indication of the functional capability of the converter to be provided. As a result, erroneous measurements due to incomplete conversion in a consumed converter can be avoided. A change of the converter is only required in case of need, which offers an advantage financially and in terms of time, since the converter cartridge is installed in the device and is changed by a service engineer.

The indication concerning the actual functional capability of the converter allows a remaining uncertainty to be eliminated.

The sensor may be coated with the at least a part of the converter material. Consequently, the converter material on the sensor behaves approximately in the same way as neighboring converter material on a carrier material surrounding the sensor. The characteristics of the neighboring converter materials consequently substantially coincide. In this way it is sufficient to record the characteristic of the converter material that is located in the recording range of the sensor in order to be able to infer the functional state of the filter.

The sensor may be arranged at a distance from the gas outlet opening in the filter housing. The distance may correspond at least to a critical packing height of the converter material ahead of the gas outlet opening. This allows the sensor to record whether the consumption of the converter material has advanced as far as the critical packing height. The critical packing height represents a distance from the gas outlet opening in the direction of the gas inlet opening. If the converter material has been consumed up to the critical packing height, the filter should advantageously be changed at an early time. The critical packing height may include a safety reserve of converter material.

The first electrode may be arranged in the region of the gas inlet opening. The second electrode may be arranged in the region of the gas outlet opening. This allows the characteristic of the entire converter material to be recorded.

The electrodes may be configured as grid electrodes or alternatively as finger electrodes. Grid electrodes may for example be arranged at the gas inlet opening and the gas outlet opening. The finger electrodes may be configured as interdigital finger electrodes and mesh alternately with one another. Thus, the finger electrodes may be at a defined spacing from one another in which the characteristic can be dependably determined.

The electrodes may be formed in a wall of the filter housing. In this way, the sensor, and any electrical leads for contacting the sensor, may be integrated in the filter housing. As a result, a separate sensor element is not required, and so the production of the filter is simplified. Moreover, a position of the sensor within the filter housing is predefined, and is consequently known.

The sensor may be configured as an impedance sensor. An impedance of the converter material may be measured by an alternating voltage between the electrodes. This allows the characteristic to represent an impedance of the converter material. Alternatively, the sensor may for example be configured as a capacitive sensor.

The filter may have an impedance recording device, which is designed for the purpose of recording the characteristic as an impedance of the at least a part of the converter material by using a signal of the sensor and reproducing it for example in an impedance value. The impedance recording device may provide an electrical supply voltage to the sensor. In particular, the impedance recording device may be designed to provide an alternating voltage with a variable frequency to the electrodes of the sensor for recording the impedance.

The filter may have a providing device, which is designed to provide a state signal that represents a functional state of the filter by using the characteristic of the converter material. For example, the providing device may be designed to record a signal that is provided by the sensor or by using the sensor and reproduces the characteristic of the converter material and to use the signal to provide the state signal. For example, the providing device may be configured as a comparing device, which is designed for the purpose of comparing the characteristic recorded by using the sensor with a desired characteristic or a threshold value. The comparing device may be designed to provide the state signal depending on a comparison result of the comparison, and the state signal may, depending on the embodiment, indicate an unconsumed or consumed state of the converter material. For example, the comparing device may be designed to provide the state signal if the characteristic lies outside a predefined tolerance range.

What is more, a respiratory air analyzer with a filter according to the approach presented here is presented. The filter may be used as an exchangeable cartridge in the respiratory air analyzer.

Furthermore, a method for monitoring a filter for a respiratory air analyzer is presented, the filter having a filter housing, in which a converter material is arranged between a gas inlet opening and a gas outlet opening, and the method having the following step:

recording a characteristic of a converter material of the filter by using a sensor, which is arranged in the filter housing and has a first electrode and a second electrode, between which the at least a part of the converter material is arranged.

The method may comprise a providing step, in which an item of information about the state of the filter and alternatively or in addition an item of information about servicing the filter is provided by using the characteristic. Such provided information, for example in the form of a state signal, allows the filter to be monitored. The monitoring can be used to change the filter when the converter material has reached a predetermined state.

BRIEF DESCRIPTION OF THE DRAWINGS

Exemplary embodiments of the disclosure are explained in more detail in the description that follows and are represented in the drawings, in which.

DETAILED DESCRIPTION

In the description that follows of favorable exemplary embodiments of the present disclosure, the same or similar designations are used for the elements that are represented in the various figures and act in a similar way, without the description of these elements being repeated.

Figure 1:
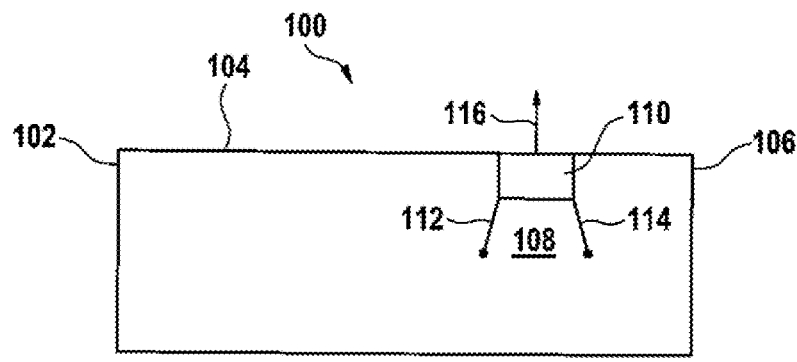
FIG. 1 shows a schematic representation of a filter for a respiratory air analyzer according to an exemplary embodiment.

FIG. 1 shows a schematic representation of a filter 100, which can be used by way of example for a respiratory air analyzer, according to an exemplary embodiment. The filter 100 is designed for the purpose of filtering an air stream in the respiratory air analyzer. The filter 100 is an exchangeable subassembly of the respiratory air analyzer and may be referred to as a filter cartridge 100.

During the operation of the respiratory air analyzer, the air stream enters a filter housing 104 of the filter 100 as an unfiltered air stream through a gas inlet opening 102 and, after the filtering, leaves the filter housing 104 as a filtered air stream through a gas outlet opening 106. Arranged in the filter housing 104 is a converter material 108. The converter material 108 is designed for the purpose of filtering the air stream. The converter material 108 may for example have been applied to a carrier material. The carrier material makes as large a surface area as possible available for the converter material 108. For this purpose, the carrier material, with the converter material 108 on it, may have been introduced into the filter housing 104 as a packing. The packing thereby completely fills at least a large part of the filter housing 104 between the gas inlet opening 102 and the gas outlet opening 106.

The converter material 108 reacts with at least one chemical species in that a constituent of the converter material 108 bonds with the chemical species and/or in that a constituent of the species bonds with the converter material 108. This has the effect of modifying the converter material 108 and the chemical species. The converter material 108 is consumed. The chemical species is converted into a wanted species or is adsorbed. An adsorption takes place for example in the case where activated carbon is used.

When the chemical species is present in the air stream, it reacts with the first unconsumed converter material 108 with which the species comes into contact. The unconsumed converter material 108 that is arranged closest to the gas inlet opening 102 is thereby consumed first. If the filter 100 is new, substantially all of the converter material 108 is unconsumed. In the course of use, the converter material 108 is consumed from the gas inlet opening 102 to the gas outlet opening. When there is only little unconsumed converter material 108 in the region of the gas outlet opening 106 in the filter 100, there is a fall in the probability that all of the species present in the air stream will come into contact with unconsumed converter material 108. Consequently, there is a rise in the probability that part of the species will pass through the filter 100 without being converted. If the air stream flows through a defined minimum section of unconsumed converter material 108, the chemical species is converted into the wanted species with an as-intended minimum probability.

In order to record an as-intended functional capability of the filter 100, a sensor 110 for sensing a characteristic of the converter material 108 is arranged in the filter housing 104. Here, the characteristic represents whether the converter material 108 is unconsumed or consumed.

The sensor 110 has a first electrode 112 and a second electrode 114. Between the electrodes 112, 114 is an intermediate space. Arranged in the intermediate space is converter material 108. The electrodes 112, 114 are used to record the characteristic of the converter material 108 between the electrodes 112, 114. The sensor 110 is designed for the purpose of reproducing the characteristic in an electrical signal 116.

Apart from the electrodes 112, 114, the sensor 110 may comprise a measuring circuit, which is designed for example to carry out an impedance measurement in response to an operating voltage applied to the sensor 110. Alternatively, for example in a way corresponding to the control electronics shown in FIG. 2, such a measuring circuit may be arranged separately from the filter 100 and be coupled with the sensor 110 by way of an interface of the filter housing 104.

The sensor 110 may be configured as a discrete component, which may have been inserted into the filter housing 104. Alternatively, the sensor 110 may be configured as part of the filter housing 104, for example in the form of an imprint of structural elements of the sensor 110 on an inner side of the filter housing 104 that is facing the converter material 108.

The part of the converter material 108 of which the characteristic can be recorded by the sensor 110 may be arranged between the electrodes 112, 114 during the filling of the filter housing 104 with the converter material 108. Alternatively, this part of the converter material 108 may be integrated or inserted into the filter housing 104 together with the sensor 110 as additional converter material 108, in the form of a component part of the sensor 110, that is to say be introduced into the filter housing 104 before or after the filling of the filter housing 104 with the actual converter material 108.

Figure 2:
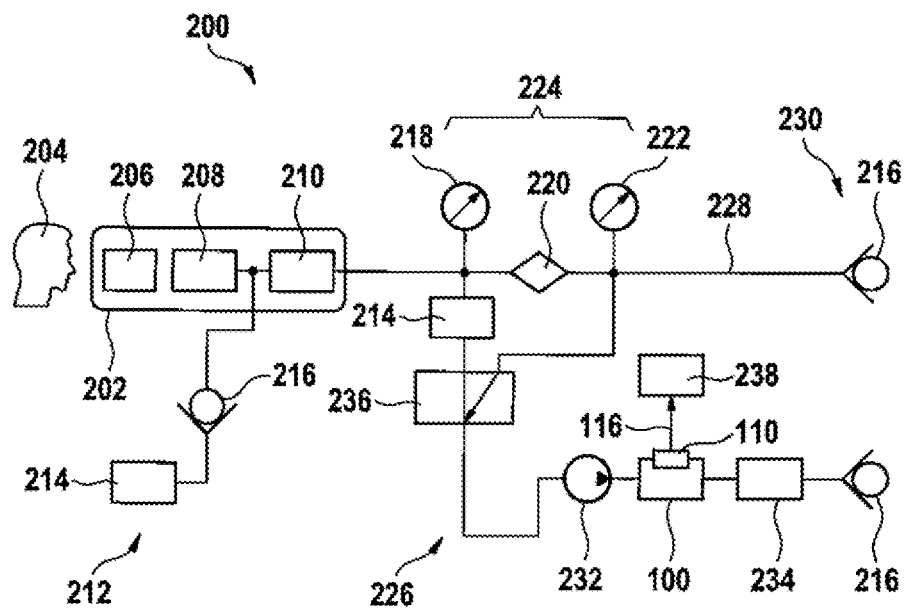
FIG. 2 shows a block diagram of a respiratory air analyzer with a filter according to an exemplary embodiment.

FIG. 2 shows a block diagram of a respiratory air analyzer 200 with a filter 100 according to an exemplary embodiment. The filter 100 in this case corresponds substantially to the filter in FIG. 1. As an overall system, the respiratory air analyzer 200 has an exchangeable mouthpiece 202, through which a patient 204 can blow an air stream into the respiratory air analyzer 200. The mouthpiece 202 has a blow-in opening 206, a bacteria filter 208 and an air dryer 210. The air stream thereby flows from the patient 204 through the blow-in opening 206, through the bacteria filter 208 and through the air drying device 210. Arranged in the air drying device 110 is a drying agent. Connected between the bacteria filter 208 and the air drying device 210 is an ambient air inlet 212. The ambient air inlet 212 has a zero air filter 214 and a check valve 216. The check valve 216 prevents respiratory air from flowing out of the mouthpiece 202 through the ambient air inlet 212.

Arranged after the mouthpiece 202 is a pressure sensor 218. The pressure sensor 218 is arranged between the mouthpiece 202 and a constriction 220. The constriction 220 produces an exhaling resistance for the patient 204.

An optional pressure sensor 222 may be arranged after the constriction 220. The pressure sensor 218 and the optional pressure sensor 222 can be used to record a differential pressure 224 at the constriction 220.

After the constriction 220, a sensor path 226 branches off from a main path 228 of the respiratory air analyzer 200. After the branching off of the sensor path 226, the main path 228 runs directly to an ambient air outlet 230, at which a further check valve 216 is arranged. The further check valve 216 prevents an inflow of ambient air into the main path 228.

Arranged in the sensor path 226 is a pump 232, which sucks a defined air stream out of the main path 228 and directs it through the filter 100 or the converter 100 to a sensor 234. After the sensor 234, the branched-off air stream is let out into the surroundings through a further ambient air outlet 230, likewise by way of a check valve 216.

Arranged before the pump 232 is a valve 236, by which a bypass with respect to the main path 228 before the constriction 220 can be switched. Arranged in the bypass is a further zero air filter 214.

Control electronics 238 of the respiratory air analyzer 200 are connected to the sensor 110 of the filter 100 and receive the signal 116. The control electronics are designed for the purpose of evaluating the signal 116 and providing a diagnostic indication on the device 200 for an operator of the respiratory air analyzer 200. For example, the control electronics 238 are configured as a providing device for providing a state signal indicating the state of the filter 100. For this purpose, the control electronics 238 may be designed to compare the signal 116 with a threshold value, in order to be able to assess the state of the converter material of the filter 100. Alternatively, the control electronics 238 may be designed to output the signal 116 as a state signal.

This allows the electrical sensor signal 116 to be used for the digital indication of whether the converter of the filter 100 is in order or not in order, to the user about the state of the converter of the filter 100, for example by way of a service indicator or a warning lamp.

Figure 3:
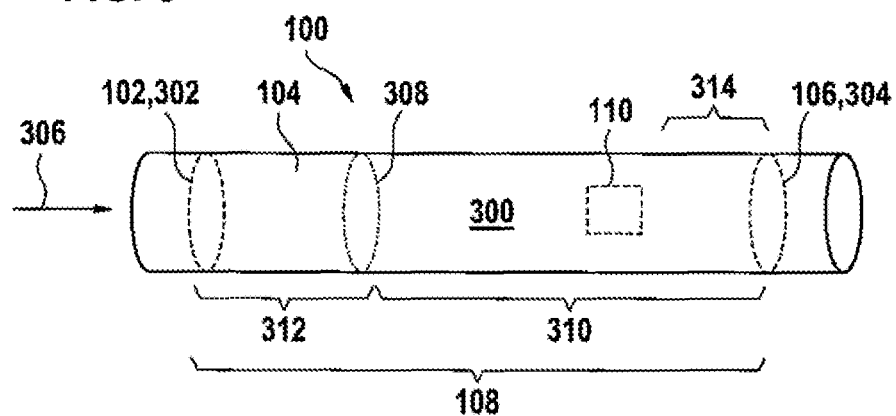
FIG. 3 shows a representation of a filter according to an exemplary embodiment.

FIG. 3 shows a representation of a filter 100 according to an exemplary embodiment. The filter 100 in this case corresponds substantially to the filter described on the basis of FIG. 1. According to this exemplary embodiment, the filter 100 has a cylindrical filter housing 104. The converter material 108 has been introduced into the filter housing 104 as a packing of a carrier material 300. Here, a fine-meshed first grid 302 is arranged at the gas inlet opening 102. Similarly, a fine-meshed second grid 304 is arranged at the gas outlet opening 106. The fine-meshed grids 302, 304 close off the filter to stop the carrier material 300 escaping from the filter 100. The air stream 306 can flow through the grids 302, 304 substantially unhindered.

During the operation of the filter 100, the air stream 306 is filtered by the converter material 108. Beginning at the gas inlet opening 102, the converter material 108 is consumed. There forms a front 308, which separates carrier material 300 with unconsumed converter material 310 from carrier material 300 with consumed converter material 312. In the course of the operating time of the filter 100, the front 308 migrates from the gas inlet opening 102 in the direction of the gas outlet opening 106. A traveling rate of the front 308 depends here on an amount of the substance to be filtered out in the air stream 306.

When the front 308 has progressed to the extent that only a critical packing height 314 of unconsumed converter material 310 remains, the filter 100 should be changed for an unconsumed filter.

For this purpose, the filter 100 has the sensor 110. The sensor is set back from the gas outlet opening 106 by the critical packing height 314. For this purpose, the sensor 110 is arranged here before the critical packing height 314, as seen in the direction of the air stream 306. The signal of the sensor 110 consequently indicates the front 308 when it has arrived just before the critical packing height 314. Thus, a small safety buffer remains, and the filter 100 can be changed at the next possible opportunity.

Tests show a spreading of the aged zone 312 in the form of a front in the direction of gas flow over the packing height of the converter 108. The sensor 110 is therefore ideally arranged in the system 100 in such a way that the arrival of the front 308 just before a functionally critical remaining packing height 314 of the converter 108 is detected, in order to ensure that the filter is changed at the right time.

Figure 4:
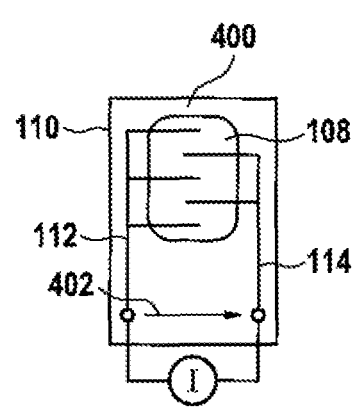
FIG. 4 shows a representation of a sensor according to an exemplary embodiment.

The transformation of the analyte at the converter material 108 has the effect that the chemical structure of the converter material 108 alters, and with it the impedance of the material 108. If a coating of a similar type is applied to a suitable transducer, for example two interdigitated comb electrodes (IDC), the remaining residual activity can be inferred by way of continuous determination of the impedance. A diagram to illustrate this principle is represented in FIG. 4.

In an exemplary embodiment, the IDC sensor area 110 and the outgoing leads are applied to the inner side of the cartridge 104, in which the converter material 108 is later located, by pad printing (polydimethylsiloxane PDMS). Leading out takes place by contacting by way of clamping that is brought about by means of a sealing material or a cover. One possible way in which this is accomplished is by a metalization divided in two on the closure plug, the halves of which respectively lead out one side of the electrode. An evaluation of the impedance measurement is performed by the device software.

Further possible ways of accomplishing this directly on the coated carrier material 300 are likewise possible. On account of the increasing impedance through the insulating carrier material, detectors 110 that can resolve impedances into the high frequency range of 100 MHz in a space-saving manner are required.

In an exemplary embodiment, the measurement takes place directly on the coated carrier material 300 by way of two opposing electrodes, for example grid electrodes. The electrodes are likewise arranged just before the critical packing height 314 on the walls of the cartridge 104, in order to detect once again the beginning 308 of the aging at this location.

In an alternative exemplary embodiment, the measurement of the impedance takes place over the entire filling height. For this purpose, the filter has a respective grid electrode 302, 304 at the beginning 102 and the end 106 of the packing 300 vertically in relation to the gas stream 306. The advancement of the aging 308 has the effect that the overall impedance of the converter packing 300 alters, until a critical value is reached. Thus, an analog indication of the functional capability of the sensor 100 is possible.

FIG. 4 shows a representation of a sensor 110 according to an exemplary embodiment. The sensor 110 in this case corresponds substantially to a sensor as it is represented in FIGS. 1 to 3. The sensor 110 has the two electrodes 112, 114, which are spaced apart from one another by converter material 108. The sensor 110 is formed as an impedance sensor 110. The electrodes 112, 114 have been printed onto a sensor carrier 400 as alternately intermeshing finger electrodes 112, 114. The converter material 108 has been applied to the sensor carrier 400 as a continuous layer over the electrodes. This results in a meandering strip of converter material 108 between the electrodes 112, 114.

When the converter material 108 is consumed, the impedance of the converter material 108 alters. The impedance or an AC resistance of the converter material 108 can be measured by applying an alternating voltage 402 to the electrodes 112, 114.

In other words, FIG. 4 shows a diagram of a coated transducer 400 with IDCs 112, 114.

Figure 5:
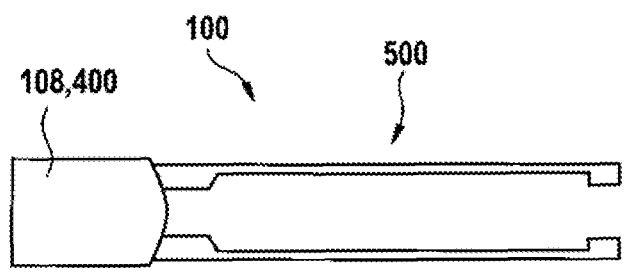
FIG. 5 shows a further representation of a sensor according to an exemplary embodiment.

FIG. 5 shows a further representation of a sensor 100 according to an exemplary embodiment. The sensor 100 corresponds substantially to the sensor in FIG. 4. Here, the sensor 100 has two legs 500, which respectively have a supply lead to one of the electrodes. The sensor carrier 400 is coated with the converter material 108 over its full surface area. Here, the electrodes lie concealed under the converter material 108.

In other words, FIG. 5 shows an image of a structure by way of example with coating of a ceramic transducer 400 (dimensions about 50×5×1 mm) with a printed-on metallic interdigital structure after coating with $KMnO_4$ 108.

The coating of the transducer element 400 with $KMnO_4$ 108 may take place for example by producing a suspension of 10 mg of $KMnO_4$ in 10 ml of acetone and applying the suspension dropwise to the transducer element 400. For example, 10 drops may be dropped on, and the sensor 100 left to dry between each drop. Thus, a layer 108 of about 10 to 100 µm in thickness can be produced.

Since the thin layer 108 on the transducer 400 behaves in a way analogous to the coating on the silica gel during aging, for integration in the system an IDC sensor 100 can for example be integrated in the filter housing in a space-saving manner.

Figure 6:
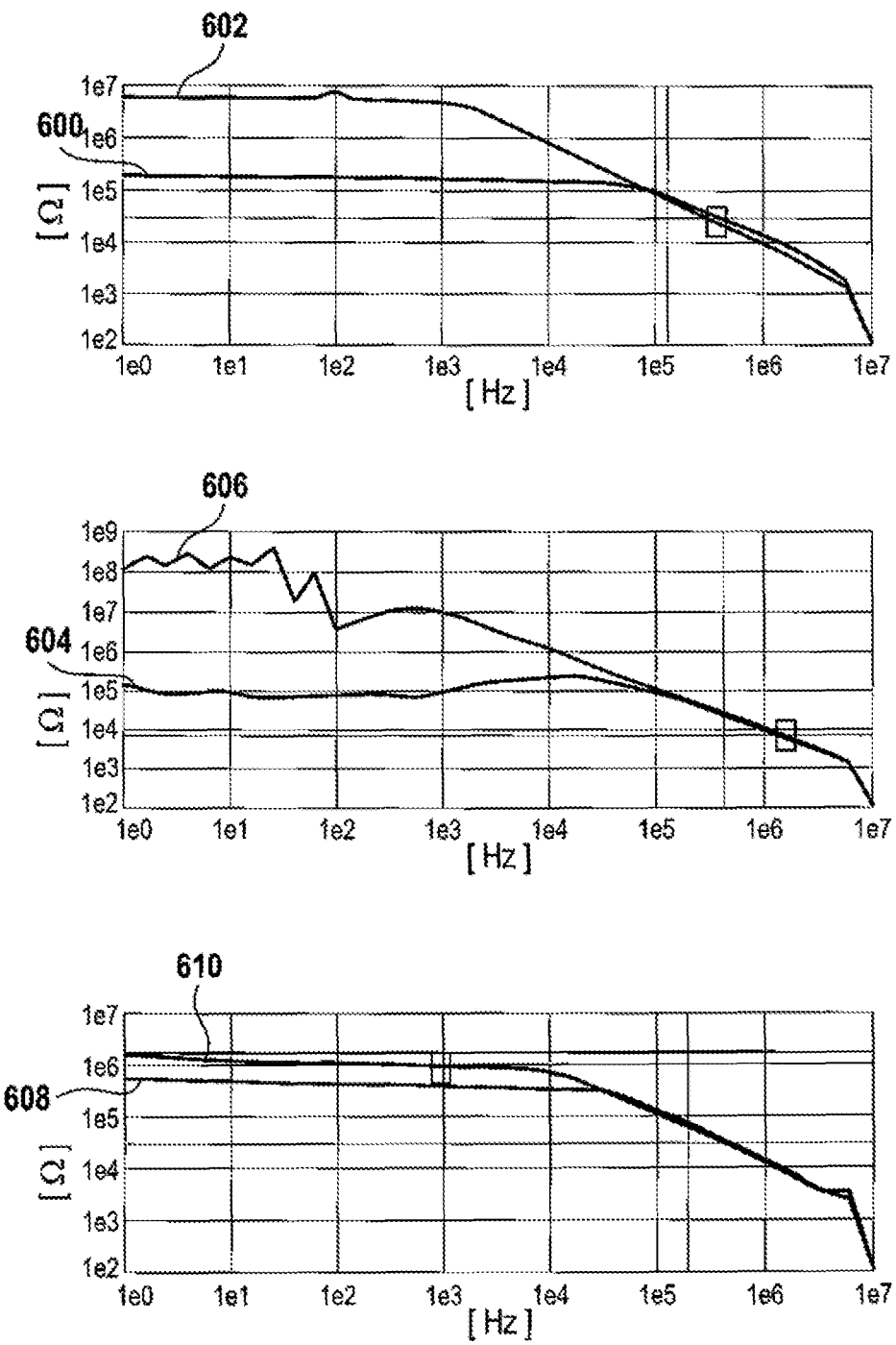
FIG. 6 shows impedance curves of impedance sensors according to an exemplary embodiment.

FIG. 6 shows impedance curves 600, 602, 604, 606, 608, 610 of impedance sensors according to an exemplary embodiment. Each two of the impedance curves 600, 602, 604, 606, 608, 610 represent an impedance sensor and are presented in a diagram together. In the diagrams, a frequency in hertz [Hz] is plotted on the x axis against an impedance in ohms [Ω] on the y axis.

The first impedance curve 600 represents the impedance of a first impedance sensor against the frequency, the converter material in the case of the first impedance curve 600 being unconsumed. In the case of the second impedance curve 602, the converter material has been consumed. A rise in the impedance in the case of consumed converter material is clearly evident, in particular at low and medium frequencies.

The third impedance curve 604 represents the impedance profile of a second impedance sensor with unconsumed converter material. The fourth impedance curve 606 represents the impedance profile of the second impedance sensor with consumed converter material. Here, too, a clear rise in the impedance in the case of consumed converter material is evident. The rise is more pronounced here at the low frequencies and less pronounced at the medium frequencies.

The fifth impedance curve 608 represents the impedance profile of a third impedance sensor with unconsumed converter material. The sixth impedance curve 610 represents the impedance profile of the third impedance sensor with consumed converter material. The curve profiles 608, 610 correspond substantially to the curve profiles 600, 602, the rise in the impedance being less pronounced here, but clearly evident.

The measured impedance increases with increasing consumption of the material or the transformation of $KMnO_4$ into $MnO_2$. In FIG. 6, Bode plots for three independently produced sensors are presented. The lower curve respectively represents the new state, while the upper curve has been traced after the aging of the sample in gas with NO.

The strength of the impedance is constantly high in the range up to 1 kHz, is increased still further by the aging and reaches the limit of the measuring range of the device used.

Figure 7:
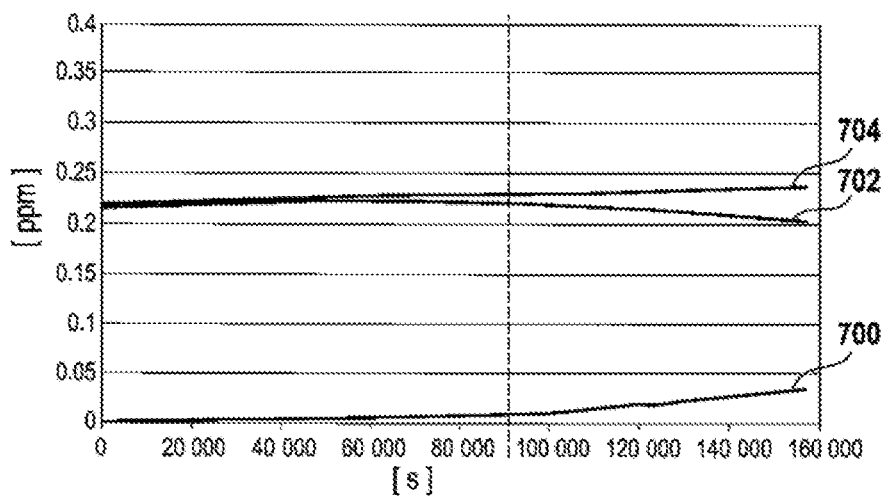
FIG. 7 shows aging curves of a converter material according to an exemplary embodiment.

FIG. 7 shows aging curves 700, 702, 704 of a converter material according to an exemplary embodiment. The aging curves 700, 702, 704 are represented in a diagram that has a time in use in seconds [s] of a filter according to the approach presented here plotted on the x axis against a gas concentration in parts per million [ppm] on the y axis. In this case, the first aging curve 700 represents a concentration of nitrogen monoxide NO in the air stream filtered by using the filter. The second aging curve 702 represents a concentration of nitrogen dioxide $NO_2$ in the filtered air stream. The third aging curve 704 represents a concentration of nitrogen oxides $NO_x$ in the filtered air stream.

The aging curves 700, 702, 704 are chemiluminescence detector (CLD) data of a measurement of silica gel coated with $KMnO_4$ by overflowing with NO-containing gas (250 ppb NO in $N_2$, gas flow 3 l/min).

In this case, the concentration 700 of nitrogen monoxide NO in the filtered air stream steadily increases over the time in use. By contrast, the concentration 702 of nitrogen dioxide $NO_2$ steadily falls. The concentration 704 of nitrogen oxides $NO_x$ remains substantially constant over the time in use. After a time in use of about 90 000 seconds, the concentration 700 of nitrogen monoxide NO exceeds a limit value. This suggests incomplete conversion of NO into $NO_2$ due to going below the critical packing height in the filter.

The aging curves 700, 702, 704 show the typical aging mechanism of $KMnO_4$ under constant overflowing with an NO-containing gas mixture and illustrate at what point the conversion of NO into $NO_2$ becomes incomplete due to going below the critical packing height.

Figure 8:
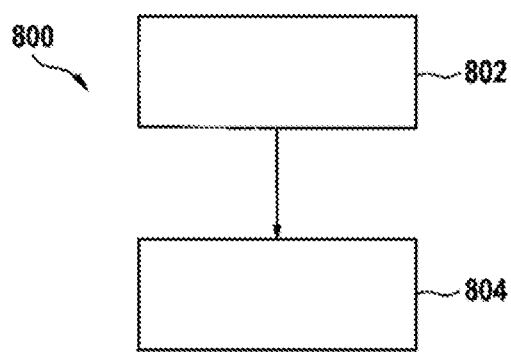
FIG. 8 shows a flow diagram of a method for monitoring a filter for a respiratory air analyzer according to an exemplary embodiment.

FIG. 8 shows a flow diagram of a method 800 for monitoring a filter or a converter for exhaled breath analysis for a respiratory air analyzer according to an exemplary embodiment. The method 800 has a step 802 of recording a characteristic of a converter material of the filter.

In an exemplary embodiment, the method 800 has a providing step 804. In the providing step 804, an item of information about the capacity of the filter and alternatively or in addition an item of information about servicing the filter is provided by using the characteristic.

If an exemplary embodiment comprises an "and/or" conjunction between a first feature and a second feature, this should be read as meaning that, according to one embodiment, the exemplary embodiment comprises both the first feature and the second feature and, according to a further embodiment, the exemplary embodiment comprises either only the first feature or only the second feature.

What is claimed is:

1. A filter for a respiratory air analyzer, comprising:
a filter housing;
a converter material arranged in the filter housing between a gas inlet opening and a gas outlet opening; and
a sensor arranged in the filter housing, the sensor having a first electrode and a second electrode configured to indicate a characteristic of at least a part of the converter material arranged between the first and second electrodes, wherein the sensor is arranged at a distance from the gas outlet opening in the filter housing, the distance selected such that variation of the characteristic by more than a predetermined amount indicates that the filter should be changed to avoid incomplete conversion by the converter material of a gas introduced into the filter.

2. The filter according to claim 1, wherein the converter material is coated onto spheres of material and coated on the sensor.

3. The filter according to claim 1, wherein the first electrode is arranged in a region of the gas inlet opening and not in a region of the gas outlet opening, and the second electrode is arranged in a region of the gas outlet opening and not in a region of the gas inlet opening.

4. The filter according to claim 1, wherein the first and second electrodes are configured as grid electrodes or finger electrodes.

5. The filter according to claim 1, wherein the first and second electrodes are formed in a wall of the filter housing.

6. The filter according to claim 1, further comprising an impedance recording device configured to record an impedance of the at least a part of the converter material by using the sensor.

7. The filter according to claim 1, further comprising a providing device configured to provide a state signal that represents a functional state of the filter by using the characteristic of the converter material.

8. The filter of claim 1, wherein:
the filter is arranged such that a gas upon entering the filter through the gas inlet opening travels along a sensor path which extends to the gas outlet opening;
the first electrode is spaced apart from the gas inlet opening and located directly between the gas inlet opening and the gas outlet opening along the sensor path; and
the second electrode is located directly between the first electrode and the gas outlet opening along the sensor path.

9. The filter of claim 8, wherein the converter material is a packing which packs a cross-section of the filter housing at a location between the gas inlet opening and the first electrode.

10. The filter of claim 1, wherein the converter material extends diametrically along a cross-section of the filter housing at a location between the first electrode and the second electrode.

11. A respiratory air analyzer, comprising:
a filter including:
a filter housing,
a converter material arranged in the filter housing between a gas inlet opening and a gas outlet opening, and
a sensor arranged in the filter housing, the sensor having a first electrode and a second electrode, wherein the converter material is coated onto spheres of material and coated on the sensor, the sensor configured to indicate a characteristic of the converter material coated on the sensor.

12. The respiratory air analyzer of claim 11, wherein:
the filter is arranged such that a gas upon entering the filter through the gas inlet opening travels along a sensor path which extends to the gas outlet opening;
the first electrode is spaced apart from the gas inlet opening and located directly between the gas inlet opening and the gas outlet opening along the sensor path; and
the second electrode is located directly between the first electrode and the gas outlet opening along the sensor path.

13. The respiratory air analyzer of claim 11, wherein the converter material is a packing which packs a cross-section of the filter housing at a location between the gas inlet opening and the first electrode.

14. The respiratory air analyzer of claim 11, wherein the converter material extends diametrically along a cross-section of the filter housing at a location between the first electrode and the second electrode.

15. A method for monitoring a filter for a respiratory air analyzer, the filter having a filter housing and a converter material coated onto spheres of material and coated on the sensor, the converter material further arranged in the filter housing between a gas inlet opening of the filter housing and a gas outlet opening of the filter housing, the method comprising:
indicating a characteristic of the converter material coated on the sensor using the sensor, the sensor having a first electrode and a second electrode and the coating of converter material on the sensor arranged between the first and second electrodes.

* * * * *